United States Patent [19]
Emerson et al.

[11] Patent Number: 5,639,794
[45] Date of Patent: Jun. 17, 1997

[54] USE OF SAPONIN IN METHODS AND COMPOSITIONS FOR PATHOGEN CONTROL

[75] Inventors: Ralph W. Emerson; Bradford G. Crandall, Jr., both of Davis, Calif.

[73] Assignee: Proguard, Inc., Suisun City, Calif.

[21] Appl. No.: 476,840

[22] Filed: Jun. 7, 1995

[51] Int. Cl.$^6$ .............................. A61K 31/11; A01G 1/00
[52] U.S. Cl. .................................. 514/699; 800/200
[58] Field of Search .............................. 514/699; 800/200

[56] References Cited

U.S. PATENT DOCUMENTS

| | | | |
|---|---|---|---|
| 2,465,854 | 3/1949 | Dorman et al. | 167/30 |
| 4,402,950 | 9/1983 | Wolf et al. | 424/195 |
| 4,477,361 | 10/1984 | Sperti et al. | 252/106 |
| 4,943,674 | 7/1990 | Houck et al. | 800/205 |
| 4,978,686 | 12/1990 | Sotome | 514/698 |
| 5,149,715 | 9/1992 | Armstrong et al. | 514/701 |
| 5,166,317 | 11/1992 | Wallace et al. | 530/350 |
| 5,175,095 | 12/1992 | Martineau et al. | 435/69.1 |
| 5,177,011 | 1/1993 | Shewmaker et al. | 435/172.3 |
| 5,202,247 | 4/1993 | Kilburn et al. | 435/195 |
| 5,290,557 | 3/1994 | Mason et al. | 424/410 |
| 5,315,001 | 5/1994 | Kridl et al. | 536/23.6 |
| 5,340,731 | 8/1994 | Kilburn et al. | 435/179 |

FOREIGN PATENT DOCUMENTS

| | | |
|---|---|---|
| 2529755 | 1/1984 | France . |
| 2697133 | 4/1994 | France . |
| 86025682 | 7/1982 | Japan . |
| 63-255203 | 10/1988 | Japan . |
| 1261303 | 10/1989 | Japan . |
| 504125 | 5/1939 | United Kingdom . |
| WO93/05159 | 3/1993 | WIPO . |
| WO93/24638 | 12/1993 | WIPO . |
| WO94/08036 | 4/1994 | WIPO . |
| WO94/24158 | 10/1994 | WIPO . |
| WO94/27434 | 12/1994 | WIPO . |

OTHER PUBLICATIONS

Bowles & Miller, *J. Food Protection* (1993) 56: 788–794.
Casey & Dobb, *Enzyme Microb. Technol.* (1992) 14: 739–747.
Elad et al., *Phytoparasitica* (1989) 17: 279–288.
Horst et al., *Plant Disease* (1992), 76: 247–251.
Ishibashi & Kubo, *Proc. Assc. Plants* (1987) 33: 122–125.
Jain & Tripathi, *Phytother. Res.* (1991) 5: 139–141.
Marston et al., *J. Ethnopharm* (1993) 38: 215–223.
Shimoyamada et al., *Agric. Biol. Chem.* (1990) 54: 2553–2557.
Westcott et al., *Ann. Entomol. Soc. Am.* (1992) 85(3): 304–309.
Yuan et al., *Fundamental & Applied Toxicol.* (1993) 20: 83–87.
Matsumoto Microbiology Laboratory, *Antimicrobial Test of Avion–M* (1982) 57–07 (full cite not available).
Frear, *Chemistry of Insecticides and Fungicides* (1942) 13: 184–191.
Ohtsuka et al., *Effects of ABION CA chemicals on vegetable diseases* (1983) 29: 48–51.
Hagiwara et al., *Chemical Abstracts* (1993) 27: 74–77.
Ishibashi et al., *Chemical Abstracts* (1987) 33: 122–125.

*Primary Examiner*—John W. Rollins
*Attorney, Agent, or Firm*—Rae-Venter Law Group P.C.

[57] ABSTRACT

Methods and compositions employing saponin as synergist in combination with a natural product, such as an aromatic aldehyde, are provided for controlling the colonization and/or growth of plant and animal pathogens, such as fungi, insects, arachnids and non-aquatic mollusks, on materials such as plants, plant parts and agricultural products before, during, after and/or processing. The invention finds use in treating agricultural crops for pathogenic organisms which colonize the surfaces of plant parts and tissues and controlling the level of toxic metabolites present in consumable products derived from plant materials, as well as reducing the health risk associated with their consumption. A method of employing saponin to kill nematodes is also provided.

37 Claims, No Drawings

1

USE OF SAPONIN IN METHODS AND COMPOSITIONS FOR PATHOGEN CONTROL

INTRODUCTION

1. Field of the Invention

The invention relates to the use of saponin as a synergist in methods and formulations for controlling the colonization and/or growth of plant and animal pathogens on a material. The invention is exemplified by the use of compositions comprising saponin in combination with cinnamic aldehyde and coniferyl aldehyde to control growth of fungi and parasitic insects which colonize the surfaces of plant parts and tissues. The invention also relates to use of saponin alone to kill nematodes.

2. Background of the Invention

Saponins are a type of sterol glycoside widely distributed in plants. The saponins have diverse biological activities finding use in agents employed as fungicides, insecticides, anticancer agents, cosmetics, food preservatives and fertilizers with growth-promoting and insecticidal effects. Further use for saponins is found in the removal of cholesterol from dairy products and as feed supplements for livestock, such as chickens, to reduce cholesterol levels in eggs and reduce manure odor. Despite these many and diverse uses, the combined effect of saponin with other compounds remains largely unexplored, most notably the combined effect of saponin with other agents having pesticidal and/or fungicidal activities.

A variety of pesticide compositions are used for controlling plant pathogens. For example, protective fungicidal sprays on a 6–7 day schedule for both rust and powdery mildew when environmental conditions favor disease development are the typical means of control. Two frequently used systemic fungicides are benomyl and triforine. However, the cost of fungicides for control of powdery mildew is high.

The older fungicides include inorganic compounds such as copper and sulphur and the organic protectants such as thiram, captom, mameb, and chlorotholonil. These compounds act only at the surface of the plant and must be present at or before appearance of the fungal pathogen in order to prevent infection. These older fungicides are multisite inhibitors i.e., they affect many metabolic activities in a fungus.

The newer fungicides tend to be highly effective organic systemics such as benzimididazoles, sterol biosystensis inhibitors, carboxanilides, and phenylamides which act internally as well as at the plant surface. In contrast to the older surface protectants, the systemic fungicides are generally effective at much lower dosages and can cure established fungal infections, a critical factor in disease management. The systemic fungicides usually act at a single target site in the fungus, interfering with specific metabolic processes that are necessary for production of all new cell material required for growth, maintenance, and virulence of the fungal organism. These preparations typically are effective only against fungal pathogens.

The use of aromatic aldehydes for treatment of both fungal and insect pathogens has been reported. However the preparations used have been reported to require the use of expensive antioxidants, and at the concentrations used, would be expected to be phytotoxic to the host plant. Such formulations also are reported to require multiple applications to ensure continued protection of the host plant.

Pesticides and fungicides are normally designed to treat or rid the host plant or material of the infesting organism. Particularly, those surfaces of a plant or plant part that are colonized by the organisms. The colonizing organisms include sap-sucking insects and pathogenic fungi; both groups are capable of inflicting severe damage to the host plant, including stunting the growth of the host plant and decreasing plant productivity, to killing the host plant.

Pathogenic insects include those insect species which are symbiotic with bacteria, such as aphids and leaf hoppers; the host insect cannot survive without the symbionts. Aphids (homoptera) possess symbiotic bacteria of the genus Buchnera in cells called mycetocytes within the hemocoel. The bacteria are transmitted directly from the maternal aphid to her offspring and aposymbiotic aphids do not occur naturally. The bacteria may provide lipids which are required for embryogenesis of the host insect but which are absent or in low concentrations in phloem sap in plants infected by the insects.

Fungi pathogenic for plants occur in most groups of fungi. A few, such as rusts, Uredinales, Phragmidrium, and powdery mildew Erysiphacea, Sphaerotheca, and downy mildew, Peronosporacea, are obligate parasites associated with specific host plants which elaborate nutrients required by the pathogen. Additionally, fungi from the genera Aspergillus, Alternaria, Fusarium, and Penicillium can contaminate food crops and their products, all of which fungi are known to produce mycotoxins such as aflatoxins, fumonosins, fusaric acid, TA/AAL toxins, zearalenone, and trichothecene, 5-butylpicolinic acid and related phytotoxic pyridine derivatives. These mycotoxins are highly toxic to a variety of species including plants and humans and can be found in commercially prepared food stuffs including milk and milk products, beans, cereals, coconuts, peanuts, sweet potatoes and commercially prepared animal feeds.

It is evident that new methods and formulations are needed to control plant and animal pathogens and the level of toxic metabolites present in consumable products and in the environment in general. The wide-spread use of pesticides, fungicides and chemical preservatives, however, has resulted in the development and evolution of resistant pathogens. As environmental and health care concerns continue to mount, it will be necessary to identify and/or develop new pesticides and fungicides to meet the environmental standards of the future. Particularly those which are natural products for consumption by animals and thus have lower animal and environmental toxicities.

RELEVANT LITERATURE

The use of saponin from agave in compositions to protect humans and other animals against pest such as mosquitoes and ticks is described in British patent application no. 9203522. Fertilizer with growth-promoting and insecticidal effects containing saponin, lignin, phosphorous, nitrogen, potassium, and rare earth metals are disclosed in Canadian patent application no. 90100605. A food preservative containing saponin from aloe woods and a p-hydroxy benzoic acid ester is disclosed in Japanese patent application no. 61065802.

The effect of butyl alcohol and urea in compositions containing saponin for use as cosmetic agent is disclosed in Japanese patent application nos. 91195986 and 05017334, respectively. The effect of various anticancer agents in compositions containing saponin is disclosed in Japanese patent application no. 05009123.

The use of compositions containing saponin from *Yucca schidigera* or *Y. Hedera helix* against non-aquatic mollusks such as snails and slugs is disclosed in U.S. Pat. No. 5,290,557. The effect of saponin on grasshopper nymphs is described by Westcott et al., (Ann, Entomol. Soc. Am., (1992) 85(3):304–309). An antifungal drug containing saponin extracts from asparagus is described in Japanese patent application no. 2157205. The antimicrobial properties of agents comprising one or more pressed juices from a variety of plants and/or solvent extracts or their condensates in acetic acid compositions are disclosed in Japanese patent application no. 91106370. The antimicrobial and pest activity of a saponin isolated from fruit pulp, tobacco, and seed are described by Okunji et al., (Int. J. Crude Drug Res., (1990) 28(3): 193–199), Gruenweller et al., (Phytochemistry (Oxf), (1990) 29(8):2485–2490), and by Lalithat et al., (Int. Pest Control (1988) 30(2):42–45), respectively. Use of a saponin from camellia leaves for the control of anthrose, rice blast, and rice helminthosporium leaf spot is described in Japanese patent application no. 61007290.

U.S. Pat. No. 2,465,854 describes an insecticidal composition containing a cinnamic aldehyde derivative. Control of Verticillium using cinnamaldehyde in the substrate in which mushrooms are grown is disclosed in U.S. Pat. No. 5,149,715. U.S. Pat. No. 4,402,950 describes the deactivation of viruses inside living human and animal organisms by application of a terpene obtainable from aromatic plants by steam application. The terpenes cited are: black pepper oil, cinnamon flour oil, cardamon oil, linallyl acetate, cinnamic aldehyde, saffol, caryon and cis/trans citrao. U.S. Pat. No. 4,477,361 describes a cinnamic compound containing an anti-microbial surfactant which is rendered substantive to the surface being washed.

The antibotulinal properties of various aromatic and aliphatic aldehyde are disclosed in Bowles and Miller (J. Food Protection (1993) 56:788–794). Other formulations which include cinnamic aldehyde have been reported to protect crops from attack by pathogenic microbes. See U.S. Pat. Nos. 4,978,686 and 5,149,715 and French patent application no. 2529755. Film-forming and/or antitranspirants coating polymers such as sodium bicarbonate and light paraffinic petroleum oils have been reported to control the level of fungal colonization. Horst et al. (Plant Disease, March 1992, p.247), Elad et al. (Phytoparasitica (1989) 17:279–288) and Ziv, et al. (Hort. Science (1993) p.124.)

SUMMARY OF THE INVENTION

The present invention relates to the use of at least one saponin as a synergist in methods and formulations comprising at least one other natural product for controlling the colonization and/or growth of plant and animal pathogens on a material. Provided is a method for controlling pathogenic organisms on plants, as well as seeds, seedlings and plants substantially free of plant pathogens. The method includes the step of contacting one or more parts or tissues of a diseased plant or a plant susceptible to attack by pathogens with an antipathogenic agent in an amount sufficient to control growth of target pathogenic organisms. Also provided are methods and compositions for controlling the level of toxic metabolites present in a variety of consumable products that are either colonized or capable of being colonized by toxin-producing microorganisms. The method includes the steps of contacting a consumable product or a precursor of such product with an antipathogenic and/or toxin reducing agent which limits the colonization of, kills or displaces one or more microorganisms which colonize the consumable material or precursor and which produce toxin(s). The invention finds use in treating agricultural crops for pathogenic organisms and controlling the level of toxic metabolites present in consumable products derived from plant materials, as well as decreasing contamination of the food chain by fungal toxins and toxic metabolites. The compositions used include aromatic aldehydes, such as cinnamic aldehyde and coniferyl aldehyde, in combination with saponin as synergist. The present invention also relates to the use of saponin alone to kill nematodes.

BRIEF DESCRIPTION OF THE PREFERRED EMBODIMENTS

Methods and formulations employing saponin as synergist in combination with a natural product, such as aromatic aldehyde, are provided for substantially controlling the colonization and/or growth of plant and animal pathogens, such as fungi, insects, arachnids and non-amphibious/non-aquatic mollusks, on materials such as plants, plant parts and agricultural products that are capable of supporting growth or otherwise being colonized and infested by pathogens. By "synergist" is intended a compound which increases the effect of at least one other compound present in a formulation whereby the combined action is greater than the sum of their separate, individual actions. By "natural product" is intended an organic compound of natural origin that is unique to one organism, or common to a small number of closely related organisms, and includes secondary metabolites of fungi and chemicals produced by plants. As an example, a fungus and/or insect colonizing surface of a plant part such as a leaf, root, or flower part, or a tissue such as xylem or phloem, is contacted with a natural product to kill, displace or otherwise retard or eliminate the growth of pathogen. By "colonizing" is intended association of a microorganism or insect with a material such as a plant part or tissue from which the pathogen derives nutrients, typically essential nutrients such as amino acids, particularly methionine. By "growth" is intended an irreversible change in an organism accompanied by the utilization of material, and resulting in increased volume, dry weight or protein content and/or increase in population or colonization. By "pathogen" is intended an organism such as a fungus, bacterium, insect, arachnid, worm and non-amphibious/non-aquatic mollusks causing damage or disease to a biological host. By "material" is intended any substance capable of supporting colonization and/or growth of a target pathogen.

The preferred method is to biocontrol pathogen infestations on plants using saponins as synergist in combination with aromatic aldehydes, particularly using naturally occurring compounds such as the aromatic aldehydes cinnamic aldehyde and coniferyl aldehyde. By "biocontrol" is intended control of plant pathogens via direct antipathogenic activity and/or induced resistance of the host plant to pathogen infestation.

The natural products can be isolated from a natural source, be wholly or partially synthetic, or be produced by recombinant techniques. The method of the subject invention is carried out by adding an effective pathogen-inhibiting amount of a compound of the invention to a plant host or to the substrate in which it is growing or is to be growing. The amount of antipathogenic agent that is applied either to the plant itself or to the rhizosphere will depend upon the degree of infestation and to some extent upon the formulation and the specific compound used and therefore must be empirically determined for best results.

The invention is suited to provide seeds, seedlings, plants, and plant parts such as fruit substantially free of pathogenic organisms such as fungi and sapsucking insects. The invention further is suited for reducing the level of mycotoxins and other toxic secondary metabolites associated with plant parts such as stems, leaves, roots, fruit, seeds, and/or flowers before, during and/or after the plant and/or plant part is harvested and/or processed for consumption.

The compositions and methods of the subject invention offer several advantages over existing compositions and methods. Although a aromatic aldehyde, cinnamic aldehyde, has been reported to exhibit antifungal properties, it has not previously been used on plants in the absence of an antioxidant or in combination with saponin. As an example, U.S. Pat. No. 4,978,686, discloses that an anti-oxidant is required for use with cinnamic aldehyde for a composition which is used for application to crops. Anti-oxidants are expensive, accordingly significant cost benefits are realized with the subject formulation. Phytotoxicity of the formulation also is decreased. In addition, a single application of cinnamic aldehyde is sufficient for long term protection of the plant host from pathogenic organisms, including both rust and powdery mildew, and is effective at lower concentrations than has been reported previously. When further used in combination with saponin, the effective anti-pathogenic properties of the aromatic aldehydes are enhanced. By identifying and exploiting the synergistic properties of saponin, the effective amount or concentration of one or more of the other formulation ingredients can be modified while preserving or enhancing the desired phytotoxic and antipathogenic effect of the formulation, particularly by allowing for a reduction in the concentration of one or more other ingredients in a given formulation. Thus, significant cost and environmental impact savings are realized. Furthermore, the long term control of pathogenic organisms results in a healthier plant and an improved yield of produce of the host plant as compared to untreated plants; the lower concentrations and single dose of antipathogenic agents decrease the likelihood of damage to the plant or its crop as well as decrease the likelihood of any adverse side effects to workers applying the pesticide, or to animals, fish or fowl which ingest the tissues or parts of treated plants.

The subject formulations also provide for effective control of both fungi and insects, eliminating the need for application of multiple agents. In particular situations, such as where an insect damages a plant part or tissue and a secondary fungal disease develops, this aspect of the invention is particularly advantageous.

Another advantage is that contamination of consumable agricultural products can be prevented or significantly decreased to a level safe for consumption. Agricultural products can be treated either preharvest or postharvest. Moreover, by treating a plant in the field with a substance which kills or displaces mycotoxin-producing fungi, the levels of toxin contamination can be significantly reduced in the harvested material. The aromatic aldehydes in particular have positive organoleptic and olfactory properties which in some eases may improve the flavor and/or smell of treated products.

DETAILED DESCRIPTION OF THE PREFERRED EMBODIMENTS

Methods and compositions employing at least one saponin in combination with at least one other natural product are used to kill, retard growth or displace pathogenic organisms, such as fungi and the various other pest such as insects and the terrestrial mollusks such as snails and slugs, from the plants or plant parts that they colonize, thereby limiting colonization and/or growth of a pathogen on the material. The compositions are applied to the plant either before it is harvested or to a plant or other material after harvest and/or processing. Most preferably, the composition is applied to the plant, plant part or tissue before harvest. The composition is preferably biodegradable and most preferably is provided as an aqueous solution or as an emulsion in a biodegradable water-soluble anhydrous non-ionic surfactant, such as Tween 80. The susceptibility of particular pathogen to the composition can be evaluated either in vitro or in vivo.

Saponins are a class of compounds, each consisting of a sapogenin portion and a sugar moiety. The sapogenin may be asteroid or a triterpene and the sugar moiety may be glucose, galactose, a pentose, or a methylpentose. S. Budavari, ed., *The Merck Index*, 11th ed., Merck & Co., Inc., Rahway, N.J., 1990, p. 1328. Saponins for use in the present formulations are a type of sterol glycoside widely distributed in plants, where each saponin consists of a sapogenin and at least one sugar moiety. The sapogenin comprises asteroid or a triterpene and the sugar moiety may comprise glucose, galactose, pentose, or methylpentose. The more preferred saponins for use in the present invention are derived yucca plants, with the most preferred being saponin extracts from *Yucca schidigera* or *Y. valida*.

Of particular interest for use in combination with saponin are the various aldehydes, particularly aromatic aldehydes which can be used for direct killing of fungal pathogens and/or for the induction of systemic plant resistance to various fungal pathogens. The method includes the step of contacting one or more parts or tissues of a diseased plant or a plant susceptible to attack by pathogens with an antipathogenic agent comprising at least one saponin as a synergist in combination with at least one growth modulating aromatic aldehyde in an amount sufficient to control growth of target pathogenic organisms. The subject formulations include the growth modulating compound as shown in formula (1) below.

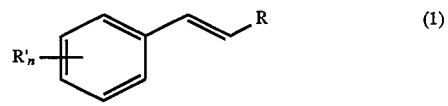

(1)

wherein R represents —$CH_2OH$ or —CHO; n is an integer from 0 to 3; and each $R^1$ independently represents OH or an organic substitutent containing from 1 to 10 carbon atoms and from 0 to 5 heteroatoms, wherein the total number of carbon and heteroatoms in all $R^1$ substitutents of said compound is no more than 15. These aromatic aldehyde compounds include natural products such as cinnamaldehyde, coniferyl aldehyde, and closely related compounds and provide a method to biocontrol pathogen infestations.

The aromatic and aliphatic aldehydes of the subject invention may be prepared by various synthetic methods known to those skilled in the art. For example, see, J. March, ed., Appendix B, *Advanced Organic Chemistry: Reactions, Mechanisms, and Structure*, 2nd Ed., McGraw-Hill, New York, 1977. Cinnamaldehyde may be prepared synthetically, for example, by oxidation of cinnamyl alcohol (Traynelis et al., *J. Am. Chem. Soc.* (1964) 86:298) or by condensation of styrerie with formylmethylaniline (Brit. patent 504,125). The subject aldehydes may also be obtained by isolation from natural sources. For example, cinnamaldehyde may be isolated from woodrotting fungus, *Stereurn subpileatum*. Birkinshaw et al., *Biochem. J.* (1957) 66:188.

A number of the aromatic and aliphatic aldehydes which find use in the subject invention, such as benzaldehyde, acetaldehyde, cinnamaldehyde, pipetonal, and vanillin are generally regarded as safe (GRAS) synthetic flavoring agents (21 CFR §172.515). These compounds have been reported to have inhibitory activity against *C. botulinum* spore germination. Bowles and Miller, *G. Food Protection* (1993) 56: 788–794. The general formula of these compounds is shown above as (1).

A preferred formulation is shown in formula (2) below.

$$(2)$$

wherein $R_1$ represents —H, —CHO, $R_2$ represents —OH or an organic substituent containing from 1 to 10 carbon atoms, and $R_3$ represents —H, a methoxy group or organic substituent containing from 1 to 10 carbon atoms. Of particular interest are aromatic aldehydes, particularly aromatic aldehydes. Examples of aromatic aldehydes of use in the present invention are cinnamic aldehyde ((3) below).

$$(3)$$

and coniferyl aldehyde ((4) below).

$$(4)$$

Aldehyde compounds of formulas (1), (2), (3) and (4) may be used either alone in combination with saponin or in combination with other active or inactive substances and may be applied by spraying, pouring, dipping, in the form of concentrated liquids, solutions, suspensions, powders and the like, containing such concentration of the active compound as is more suited for a particular purpose at hand. They may be applied, for example, in the form of dilute solution, in a suitable solvents directly to the rhizosphere either as part of an irrigation schedule or as a separate application. Combination of the aldehyde and saponin compounds may be accomplished as single or multiple components for a given formulation and in one or more steps at any suitable stage of mixing and/or application. The combination of components is preferably adapted for a particular application for a desired end result.

For use as a foliar spray, although the aldehyde can be formulated alone, it can be rendered substantive by including an emulsifier such as Tween 80. Other detergents which can be used include anionic detergents such as those described in U.S. Pat. No. 4,978,686. Generally, detergents in the formulation do not detract from the antifungal properties of the aromatic aldehydes but do increase the substantive properties of the formulation. See for example, U.S. Pat. No. 4,477,361. Additional components such as an aqueous preparation of a salt of a polyprotic acid such as sodium bicarbonate, sodium sulfate, sodium phosphate or sodium biphosphate can be included in the formulation, to increase the antifungal properties of the formulation. The resulting emulsion is diluted to an appropriate concentration for use.

Other compounds can be used alone or in combination with the compositions, for example $H_2O_2$, which is known to kill particular fungi such as *A. flavus* in alkaline environments. An antifreezing component such as glycerol, propylene glycol, ethylene glycol and/or isopropyl alcohol, and a gum or gum-like material as xanthan gum, acacia gum, gelatin, hydroxypropyl methyl cellulose and the like may also be included such as those described in U.S. Pat. No. 5,290,557. Additionally, for use preharvest, compounds which induce non-systemic or systemic plant resistance to various fungi may be used to control colonization and/or growth of certain fungi under field conditions.

The most effective amount for compositions including compounds of formula (3) and/or formula (4) as well as the amount of other compounds of formula (1) which may find use can be determined empirically using protocols known to those skilled in the art. Generally, an effective growth modulating amount of one or more compounds of formula (2) is 0.01 g/l to 25 g/l. When using saponin as a synergist in combination with an effective growth modulating amount of one or more of the aromatic compounds, an effective amount of a saponin generally is about an equivalent in activity of a saponin extract control from *Y. schidigera* comprising 0.01% to 3% v/v and preferably about 2% v/v aqueous solution of 10° brix saponin extract.

In order to determine the susceptibility of particular target fungi or insects to the claimed compositions, in vitro and in vivo tests such as are described in the Examples can be used. In particular, the mean disease control can be calculated for particular pathogens on a given material and in particular plants. The change in the infestation rating (pre and post treatment is calculated as the mean percentage of disease control (IVIPDC). MPDC is defined by the formula:

$$MDIC = \frac{(MDIC - MDIT)}{MPDC} \times 100$$

and

MDIC=Mean % of disease incidence in untreated controls
MDIT=Mean % of disease incidence in the treatment
Generally it is desirable to obtain a mean disease resistance of 60% or better, preferably at least about 70%.

The formulations also need to be evaluated for phytotoxicity, particularly when used on plants. It therefore is important that at least one evaluation of the toxicity of the formulations be on living plants of the host variety. Phytotoxicity can be rated as follows in order of increasing severity of toxicity: 0-plants without any symptoms; 1-very slightly browning of hypocotyl (no other symptoms); 2-some wilting of plant, dying of lower leaves, some browning of vascular system; 3-wilting of entire plant, leaves dying, hypocotyl with external and internal symptoms; 4-necrosis of stem, plant dying. When used on plants, it is further preferred that the formulation used have a phytotoxicity rating of 2 or less, more preferably 1 or less.

Accordingly, these and the protocols of the Examples can be used to optimize each formulation for specific pathogens using any of the compounds encompassed by formula (1) in combination with saponin as well as for use on specific plants to minimize phytotoxicity while maximizing the antipathogenic effect of the formulation. Of course each formulation can be optimized for specific pathogen and/or material, particularly plant material either pre- or postharvest, with the combination and effective amount of each component adapted for a particular application to minimize toxicity while optimizing and preferably increasing the antipathogenic effect of the formulation.

Optimization of each formulation can be achieved as desired by including at least one compound other than saponin to increase the effect of at least one other compound present in the formulation. Preferably, the combined action is greater than the sum of their separate, individual actions. The obtained compositions are advantageously optimized for either or both the phytotoxicity effect (phytotoxicity rating of 2 or less, with 1 or less preferred) and the antipathogenic effect of the formulation (mean disease resistance of 60% or better, with a least about 70% or greater preferred). It is even more preferable that phytotoxicity is minimized while the antipathogenic effect of the formulation is increased. Of particular interest is optimization of the formulation to increase the mean disease resistance against a broad range of pathogens. In another embodiment, the formulation ingredients are modified to optimize the antipathogenic and toxin reducing effect of the formulation and/or to further reduce the phytotoxic effect of a formulation for application to various plants and plant parts preharvest. Of particular interest is the development of formulation to allow for an overall reduction in the concentration of one or more other ingredients in a given formulation while maintaining overall efficacy of the formulation. Combinations of ingredients can be accomplished as addition of single or multiple components in one or more steps at any suitable stage of mixing and/or application. The combination of components is preferably adapted for a particular application for a desired end result.

The most effective amount and combination for compositions which include saponin and at least one of the compounds of formula (1), (2), (3), (4), an emulsifier, and a salt of a polyprotic acid, for use in the invention can be determined empirically. As an example, various concentrations of saponin can applied as a separate spray to a plant in applications which employ a series of formulations containing variable amounts of a given aromatic aldehyde and/or other component. Generally, an effective amount of a saponin is measured as about an equivalent in activity of a saponin extract control from *Y. schidigera* comprising about 0.05% to 3% v/v and preferably about 2% v/v aqueous solution of 10° brix saponin extract.

In addition to saponin and the specific compounds of the formulas (1), (2), (3), (4) set forth above, derivatives of any of these compounds that produce a compound of the formula identified above upon action of a biological system on the derivative are considered to be equivalent to compounds of the invention. Thus application of precursor compounds to plant parts or tissues or harvested materials would be equivalent to the practice of the present invention. Biological conversion of precursor compounds into aromatic aldehydes is described in, for example, U.S. Pat. No. 5,149,715 and references cited therein. See also Casey and Dobb, *Enzyme Microb. Techol,* (1992) 14:739–747. Moreover, a variety of structurally related saponins are known, the most variable structural feature being the glycosylation pattern. S. Budavari, ed., *The Merck Index,* 11th ed., Merck & Co., Inc., Rahway, N.J., 1990, p. 1328. Saponins also may contain additional modifications, such as the sarasaponins which are saponins with asteroid attached, and saponin structure can be modified by any number of enzymatic, chemical and/or mechanical means known in the art. Accordingly, derivatives of these compounds which produce a formulation having the desired antipathogenic and phytotoxic reducing effect are considered equivalents of the invention.

A variety of structurally related saponins are known, the most variable structural feature being the glycosylation pattern. Saponins also may contain additional modifications, such as the sarasaponins which are saponins with asteroid attached, and saponin structure can be modified by any number of enzymatic, chemical and/or mechanical means known in the art. Saponins from *Yucca schidigera* contain steroidal saponins with the major sapogenins being sarsapogenin and tigogenin. The sarsaponin yields on hydrolysis, sarsasapogenim (sarsasapogenim 5-beta, 20-betaF, 22-deltaF, 25-betaF; also known as spirostan-3-beta-01 and parigenin), glucose and galaclose. The sarasapogenim has a molecular formula of $C_{27}H_{44}O_3$. Nobel, Park S., Agaves, Oxford Univ. Press, New York, 1994.

Accordingly, derivatives of these compounds which produce a formulation having the desired antipathogenic and/or phytotoxic effect are considered equivalents of the invention. Depending on its structure, a given saponin can have a particular pesticidal property and lend use with the present formulations. Generally an effective amount of saponin is of the range of about 0.1 to 3% and most preferably about 2% v/v aqueous solution of 10° brix saponin extract. 10° brix is a term of art in sugar chemistry. The brix degrees equals the percent by weight of sugar in the solution. Hawley, ed., The Condensed Chemical Dictionary, 10th ed., Van Nostrand Reinhold, New York, 1981, p. 149.

Depending on its structure, a given saponin can have a particular property and find use with the present formulations. Generally, saponins can be used in a variety of formulations, for example, as insecticides, fungitides, biocides generally, surfactants, emulsifiers, flavorings and feed supplement formulations. These diverse activities are attributable to the chemical make up of a particular saponin and most typically dependent on the source form which the saponin is derived. For example, saponins derived from Japanese Camellia control the growth of mosquito larvae. Saponins from sources other than Yucca plants can be used as active agents in insecticidal compositions. Saponins from Yucca plants are used to remove cholesterol from foodstuffs and as a biocidal treatment and anti-caking/emulsification agent for waste sludge and other biomass systems. Sarasaponins derived from agave plants, for example, find use as wetting agents and with other compounds for the treatment of human fungal diseases. Of particular interest are the use of saponins as synergist to increase the effect of at least one other compound present in a formulation for application against various pathogens, toxin producing microorganisms or their toxic metabolites whereby the combined action of the formulation ingredients is greater than the sum of their separate, individual actions and/or range of activity. It is preferable to select a saponin that optimally increases the antipathogenic and toxin reducing effect of the formulation. A saponin affording such activity is most preferably selected for combination with at least one of the compounds of formula (1), (2), (3), (4), an emulsifier, such as Tween 80, and/or a salt of polyprotic acid, such as sodium bicarbonate, using the protocols described in the Examples.

The saponins for use in the present invention can be produced and/or isolated from various plant parts including fruit, leaf, seed and/or root, using means known in the art, from a variety of sources including the various plants known to produce them, ranging from yucca, quillaja, agave, tobacco, licorice, soybean, ginseng and asparagus to aloe woods. Saponins for use in with the present invention are preferably non-toxic to humans and higher animals. Most preferably the saponin for use in the present invention is non-toxic food grade, the source being from yucca plants. Even more preferred are the saponins from *Yucca schidigera* or *Y. valida* and their equivalents.

For applications where the formulation is to be used to prepare the ground or other growth substrate for planting of host plants susceptible to particular pathogens, to apply to an already infested growth substrate, or to harvested material the formulations of the subject invention can be added directly to the rhizosphere, the substrate or the harvested material, or they can be bound to a solid support or encapsulated in a time release material. The aldehyde components can be coupled to a solid support, optionally through a linker such as a polysaccharidase binding domain, where the solid support is a polysaccharide such as cellulose, particularly microcrystalline cellulose. The preparation of cellulose binding domains is described in U.S. Pat. Nos. 5,340,731; 5,202,247 and 5,166,317. The aldehydes can be coupled to the binding domains, with or without a clearable bond, using methods well known to those skilled in the art. Examples of delivery systems include starch-dextran, and the like. See Yuan et al., *Fundamental and Applied Toxicology* (1993) 20: 83–87, for examples of delivery systems. Where a solid carrier is used, materials which can lead to oxidation of the active aldehydes should be avoided.

The method of the present invention is carried out by introducing into a target pathogenic organism a sufficient amount of an anti-pathogenic agent to impair growth and/or viability of the target pathogenic organism. A formulation containing the antipathogenic agent is introduced to a plant tissue or part either pre- or postharvest. For example, the formulation is sprayed on as a wet or dry formulation to the surface and/or underside of the leaves or other plant tissue or part of a plant infected with a plant pathogen, or of a plant susceptible to infestation with a plant pathogen to the point of run off. The plants can be sprayed prior to or after infestation, preferably prior to infestation. However, in order to minimize damage to the host plant, where feasible, it is preferable to treat older plants, as young green leaves tend to be more susceptible to phytotoxicity. Alternately, the formulation can be applied wet or dry to the rhizosphere where it can contact the roots and associated pathogenic organisms which colonize the roots. In some instances, time-release formulations may find use, particularly for applications to the rhizosphere, or to postharvest materials.

The method of introducing into the target organism can be by direct ingestion by the pathogenic organism, for example, an insect or a fungus from a treated plant surface, or by feeding of a pathogenic organism on a nutrient-providing surface of a host entity which is colonized by the target pathogenic organism. The presence of the anti-pathogenic agent on a nutrient-providing surface of a host plant can be a result of direct contact of the anti-pathogenic agent with the plant part or it can be by elaboration from the host plant as a result of induction of systemic resistance as a secondary effect to prior treatment of the plant with the anti-pathogenic agent.

In addition to treating a host plant, seeds can also be treated using the subject formulations. The seeds can be dusted with a powder preparation (.see U.S. Pat. No. 4,978, 686 for examples of inorganic materials to which the formulations can be adsorbed) or admixed in a plant substrate such as vermiculite. Seedlings grown under sterile conditions from treated seeds are free of susceptible fungi and insects. Additionally, seedlings also can be treated with the subject formulations. In some instances it may be necessary to adjust the treatment formulation so as to reduce any phytotoxicity associated with the treatment as tender young shoots are more likely to exhibit phytotoxicity symptoms.

In another embodiment, one or more compounds of the present formulations can be introduced to the target organism by modulating the expression of a gene encoding an enzyme required to control the level of the compound of interest in a plant, plant part, plant cell, specific plant tissue and/or associated with a particular stage of plant growth. It is of particular interest to modulate expression of either an endogenous plant gene or a transgene supplied exogenously to the plant. An "endogenous gene" is one that is normally present in the wild-type genome of the plant host of interest. A "transgene" is one that is exogenously introduced into a plant or plant part of interest through transgenic means known in the art. By "modulation" of gene expression it is intended that production of a gene product of interest can be controlled at the level of transcription, translation and/or post translation. The level of the compound of interest is controlled by modulating the expression of one or more endogenous genes or transgenes encoding one or more enzymes required to synthesize the compound of interest. Most preferable is a gene encoding an enzyme required to metabolize a precursor required for the synthesis of saponin, cinnamic and/or coniferyl aldehyde.

Methods for modulating gene expression in plants are known in the art. Variation in growth conditions or exogenous application of compounds to a plant can effect gene expression. For example, the formulations of the present invention can be used to induce systemic plant resistance through modulation of endogenous gene expression. At the molecular level, gene expression depends substantially on the transcription, translation and termination control regions which regulate expression of a structural gene coding region. By exploiting the plant signals which regulate these control regions or by the direct recombinant manipulation of the control regions, expression of a gene encoding an enzyme required to control the level of saponin, for example, can be modulated. For use in a transgene supplied exogenously to a plant host, the transgene will include control regions that are selected and designed to achieve the desired level and timing of gene expression. As appropriate, the control regions may be homologous (native) or non-homologous (non-native) to the gene of interest. By "homologous" is intended that the control region(s) is from or substantially similar to a control region normally associated with the gene of interest. By "non-homologous" is intended that the control region(s) originates from a different nucleotide source or sequence or is substantially different from the control region(s) normally associated with the gene of interest. For example, if the enzyme coding sequence is non-homologous in source as compared to the control regions, in order to have expression of the gene in a plant cell of interest, transcriptional and transnational initiation regulatory regions or promoters functional in these plant cells must be provided operably linked to the coding sequence. Transcription and translation initiation signals functional in plant cells include those from genes which are present in the plant host or other plant species, and direct constitutive or selective expression in a plant host. Of particular interest are the gene control regions that selectively regulate structural gene expression in a plant, plant part, plant cell, specific plant tissue and/or associated with a particular stage of plant growth. Preferred are those control regions that are known in the art, and in particular, transcriptional control regions or promoters that can be used to modulate the expression of a gene encoding an enzyme required to control the level of saponin, cinnamic and/or coniferyl aldehyde in a plant, plant part, plant cell, specific plant tissue and/or associated with a particular stage of plant growth. For example, promoters showing differential expression patterns in fruit are described in U.S. Pat. Nos. 4,943,674 and 5,175,095; seed in U.S. Pat. No. 5,315,001; rapidly developing tissues and tender shoots in U.S. Pat. No. 5,177,011.

A preferred method for producing a desired component of the present formulations in a plant host is through recombinant DNA means. Particularly by modifying the level of at least one compound of interest of the formula (1), (2), (3), (4) and saponin in plant tissues of interest through construction of transgenic plants using recombinant techniques known in the art. The methods involve transforming a plant cell of interest with an expression cassette functional in a plant cell comprising as operably linked components in the 5' to 3' direction of transcription, a transcriptional and transnational initiation regulatory region, joined in reading frame 5' to a DNA sequence encoding one or more enzymes capable of modulating the production and/or required to produce the compound of interest, and transnational and transcriptional termination regions. Expression of an enzyme required to produce the compound of interest provides for an increase in the compounds' production as a result of altered concentrations of the enzymes involved in the compounds' biosynthesis. Of particular interest is the selective control of saponin, cinnamic and/or coniferyl aldehyde production in plant tissues such as leaves, roots, fruits and seeds.

Transgenic plants having an increased ability to accumulate aromataic aldehydes such as cinnamaldehyde and coniferyl aldehyde to provide self-protection against plant pathogens or be used as a natural source of aromatic aldehydes for extraction and subsequent use as a chemical pesticide can be prepared as follows.

Accumulation of aromatic aldehydes can be achieved by downregulating the expression of specific plant genes that encode enzymes which either cause further metabolism of the desired aldehydes or divert metabolic intermediates away from the desired aldehydes. In the case of cinnamaldehyde, for example, this involves downregulating the expression of cinnamate 4-hydroxylase (CA4H) and cinnamic alcohol dehydrogenase (CAD). CA4H ordinarily diverts some cinnamic acid away from cinnamaldehyde to produce p-coumaric acid, itself a metabolic intermediate. Reducing CA4H activity alone is not sufficient to cause accumulation of cinnamaldehyde because CAD can rapidly convert cinnamaldehyde to cinnamyl alcohol, which then becomes incorporated into lignin or accumulates as glycosides. Simultaneously reducing both CA4H and CAD activities results in increased metabolic flux from cinnamic acid into cinnamaldehyde and decreased conversion of cinnamaldehyde into cinnamyl alcohol. Some cinnamaldehyde becomes incorporated into lignin but cinnamaldehyde (either free or as glycosides) also accumulates to above-normal levels, particularly at times when the biosynthesis of cinnamic acid is elevated. This occurs when the level of phenylalanine ammonia lyase (PAL; the first and rate-limiting step in general phenylpropanoid metabolism, Hahlbrock and Scheel, (1989) *Annu. Rev. Plant Physiol. Plant Mol. Biol.* 40:347–369) activity is high, a situation that naturally occurs in plants in response to a wide range of stimuli including invasion by fungal pathogens and mechanical damage associated with wounding and insect feeding.

Inhibiting CAD activity in transgenie plants has been proposed as a method of reducing lignin synthesis in plants and thereby improving the digestibility of fodder crops (WO 93/05159). These experiments suggested that lignin biosynthesis had been altered qualitatively, but not necessarily quantitatively, but did not demonstrate or appreciate the desirability of accumulating cinnamaldehyde as a method of increasing protection against pathogens.

A number of plant CA4H and CAD genes have been cloned and their sequences are available from GenBank. Portions of these genes that include nucleotide sequences that are conserved between different plant species can be used directly in a plant expression vector (antisense or sense orientation) to suppress the expression of the corresponding endogenous genes (e.g., Pear, et al., *Antisense Res. and Develop.* (1993) 3:181–190, Napoli, et al., *The Plant Cell* (1990) 2:279–289. More preferably, these conserved gene sequences are used to isolate CA4H and CAD cDNA clones from a cDNA library of the plant species that is to be modified. The resulting cDNA clones, or portions thereof, are then introduced into a plant expression vector (antisense or sense) and used to transform the plant(s) of interest. DNA constructs according to the invention preferably comprise a sequence of at least 50 bases which is homologous to the endogenous CA4H or CAD genes.

A recombinant DNA molecule can be produced by operatively linking a vector to a useful DNA segment to form a plasmid that can be used for plant transformation. A vector capable of directing the expression of RNA from a cloned portion of a gene is referred to herein as an "expression vector." Such expression vectors contain expression control elements including a promoter. Typical vectors useful for expression of genes in higher plants are well known in the art and include vectors derived from the Ti plasmid of *Agrobacterium tumefaciens* described by Rogers et al., *Methods in Enzymology* (1987) 153:253–277. A common promoter that is used to provide strong constitutive expression of an introduced gene is the cauliflower mosaic virus (CaMV) 35S promoter (available from Pharmacia, Piscataway, N.J.). Either constitutive promoters (such as CaMV 35S) or inducible or developmentally regulated promoters (such as the promoter from a PAL gene or the endogenous CA4H or CAD genes) can be used. Use of a constitutive promoter will tend to affect functions in all parts of the plant, while use of an inducible or developmentally regulated promoter has the advantage that the antisense or sense RNA is only produced in the tissue and under the conditions it is required. The use of developmentally regulated promoters is preferred in the use of this invention because the down-regulation of phenylpropanoid biosynthesis is known to be capable of producing undesirable side-effects on the development of transgenie plants containing a heterologous PAL gene (Elkind et at., (1990) *Proc. Nat. Acad. Sci.* 87:9057–9061.

A number of different transformation methods are available for the routine transformation of a wide range of plant species. One method that is particularly efficient for the transfer of DNA into dicotyledonous plants involves the use of Agrobacterium. In this method the gene of interest is inserted between the borders of the T-DNA region that have been spliced into a small recombinant plasmid with a selectable marker gene (for example encoding neomycin phosphotransferase II or phosphinothricin acetyltransferase). The recombinant plasmid is then introduced into an Agrobacterium host by transformation or triparental mating. The Agrobacterium strain carrying the gene(s) of interest is then used to transform plant tissue by co-culturing the bacteria with an appropriate plant tissue (e.g., leaf disc). Transformed cells are selected in tissue culture using the appropriate selection agent and plants are then regenerated (see Horsch et al., (1985) *Science* 227: 1229–1231. Other methods that have been used in the transformation of plant cells, and in particular the more recalcitrant crop plants, include biolistics and electroporation (for detailed protocols, see Sanford, et al., (1993) *Methods in Enzymology* 217:483–509; and Potter, (1993) *Methods in Enzymology* 217:461–478.

Once transgenic plants have been produced, conventional enzyme assays for CA4H and CAD are used to determine the level of suppression of enzyme activity achieved in different transformants. It is likely that only a small fraction of the transformants produced will have a sufficiently low residual enzyme activity to cause the accumulation of aromatic aldehydes without also producing some undesirable side effects on plant development. For this reason, a preferred method of producing the desired transformants with both CA4H and CAD suppressed is to introduce the two genes separately into different transformants and then combine them by standard sexual crosses. This permits a larger number of combinations of level of gene suppression to be evaluated at the same time.

An alternative to overproducing aromatic aldehydes in transgenie plants is to use the plant genes to confer on a microbial host the capability of synthesizing specific aromatic aldehydes. The resulting microbes may be used either to produce the aromatic aldehydes in a fermentation system or as a natural delivery system of the aromatic aldehydes in viable or non-viable microbial preparations. Yeasts, especially *Saachoromyces cerevisiae*, are preferred organisms for this purpose because they have already been engineered for high-level expression of PAL (Faulkener, J. D. B. et al., Gene 143: 13020, 1994) and a plant cinnamate 4-hydroxylase has been shown to function in yeast (Urban, et al. 1994 *Eur. J. Blochem* 222:843–850.

The expression of PAL introduces the capability to produce elnammic acid from phenylalanine. Two additional enzymic steps are required to produce cinnamaldehyde from phenylalanine. In plants, these steps are catalyzed by the enzymes cinnamate:CoA ligasc (CL) and cinnamoylCoA reductase (CCoAR) but as 4-coumarateCoA ligase (4CL) can also use cinnamic acid as substance (Knobloch, and Hahlbrock 1977, *Arch. BioChem. Biophys.* 184:237–248, 4Cl can be used instead of CL. More than 20 cloned PAL genes and more than 6 4CL genes have been described in sufficient detail (GenBank) to facilitate their use in practicing the current invention. A gene for a CCoAR is obtained by applying standard gene cloning techniques to isolate a cDNA clone using as a probe sequence derived from the amino acid sequence of the N-terminus, or peptide fragments, of the purified protein. CCoAR has been purified and partially characterized from soybean cultures (Wengenmayer et at., (1976) *Eur. J. Biochem.*, 65:529–536; Luderitz, and Grisebach, *Eur. J. Biochem*, 119:115–124, 1981), spruce cambial sap (Luderitz, and Grisebach, supra), poplar xylem (Sarni, et al., *Eur. J. Biochem*, 139:259–265, 1984) and differentiating xylem of *Eucalyptus gunnii* (Goffner, et al., *Plant Physiol.* 106:625–632, 1994). The preferred method of purification is that of Goffner et al. (supra) because it results in a single protein band on SDS-polyacrylamide gels that an be used for protein sequencing.

The cloned genes are introduced into standard expression vectors and used to transform a microbial host, preferably yeast, by standard transformation techniques such as electroporation (Becker, and Guarante, *Methods in Enzymol*, 194:182–187, 1991). Standard enzyme assays are used to contain the functional expression of the engineered genes and assays for aromatic aldehydes are used to select strains with maximal production. Because aromatic aldehydes have antimicrobial properties it is preferred to use expression vectors that will cause expression of the introduced genes only late in the growth cycle or in response to a chemical inducer. It may also be desirable to grow the engineered microbial host in an immobilized whole cell reactor (e.g., Evans, et al., *Biotechnology and Bioengineering* 30: 1067–1072, 1987) to prevent the aldehydes from accumulating in the culture medium.

For saponin biosynthesis in a tissue of interest, plant cells are transformed with an expression cassette comprising DNA encoding a structural gene for one or more enzymes required to synthesize saponin and capable of increasing the amount of saponin in the tissue of interest. Similarly, for selective control of cinnamic and/or coniferyl aldehyde biosynthesis in a tissue of interest, plant cells are transformed with an expression cassette comprising DNA encoding a structural gene for one or more enzymes required to synthesize cinnamic and/or coniferyl aldehyde and capable of increasing the amount of these aldehydes in the tissue of interest. Of particular interest are those genes encoding one or more enzymes capable of metabolizing a precursor compound required for the biosynthesis of the saponin, cinnamic and/or coniferyl aldehyde compound of interest from substrates normally found in a plant cell. More particularly is the transgenie expression of at least one compound of the formula (1), (2), (3), (4) and saponin.

DNA constructs for expressing a gene of interest may be prepared which provide for integration of the expression cassette into the genome of a plant host. Integration can be accomplished using transformation systems known in the art such as Agrobacterium, electroporation or high-velocity microparticle-mediated transformation. Depending upon the application, saponin or one of the other compounds of interest can be preferentially expressed in a tissue of interest and/or a particular organelle. Tissue specificity is accomplished by the use of transcriptional regulatory regions having the desired expression profile. Translocation of the enzyme to a particular organelle is accomplished by the use of an appropriate translocation peptide. Methods for tissue and organelle specific expression of DNA constructs have been described are known in the art.

To verify regulation and expression of the gene of interest, various techniques exist for determining whether the desired DNA sequences present in the plant cell are integrated into the genome and are being transcribed. Techniques such as the Northern blot can be employed for detecting messenger RNA which codes for the desired enzyme. Expression can further be detected by assaying for enzyme activity or immunoassay for the protein product. Most preferably the level of the compound of interest present in a plant host is measured using methods known in the art. A desired phenotype, for example, is increased saponin content in a plant tissue of interest as measured by expression of the gene of interest and/or the level of saponin present in the plant host as compared to a control plant.

For introduction of one or more compounds of the present formulations to the target organism, a plant host expressing a gene encoding an enzyme required to control the level of the compound of interest results in the exposure of a target organism to at least one component of the antipathogenic formulation. In another embodiment, selective expression of the gene of interest induces systemic plant host resistance to pathogen attack or colonization. In a preferred embodiment, at least one component of the antipathogenic formulation is expressed by the plant host and at least one component of the antipathogenic formulation is exogenously applied to the plant host so that the combination elicits the desired phytotoxic and antipathogenic effect when either directly or indirectly introduced to the target organism. Examples of suitable plant hosts include grasses, trees, ornamental plants and the like. Other plant host include agricultural crops such as tobacco, rice, corn, strawberries, tomato, melons, banana, soybean, sunflower, peanut, maize, cotton, oil rapeseed, safflower and the like.

The target pathogenic organisms include fungi that colonize a surface of a part of a plant which provides nutrients required by the fungus. Of particular interest are those fungi which produce fumonosins and fusadc acid and their structural analogues. Examples of fungi and the plant parts which the colonize are as follows. Black spot on fruit; *Fusarium sp.* on flowers roots and leaves; and *Fusarium sp.* and *Aspergillus* on roots and leaves. Fusarium causes vascular wilts of annual vegetables and flowers, herbaceous perennial ornamentals, plantation crops and the mimosa tree. Different plants are attacked by special forms or races of the fungus. Verticulum (V. albo-atrium and V. dahlise) cause vascular wilts and colonize roots, flowers and leaves. In addition the following also constitute target organisms: *Phragmidium spt; Diplocaopan rosae; Sphaerotheca tannosa; Oibiapsis sicula; Phytophoya taraesitica; Puccinia spp; Alternaria sp; Susaiun SPP; Botrytis cinera; Sclerotinia Homoeocarca;* Dutch Elm disease (*Ceratocystis ulmi*) and oak wilt (*C. fagacearum*). Ceratocystis causes vascular wilts, mainly of trees.

Target organisms also include insects, particularly those of the orders Orthoptera; Thysanoptera which includes thrips; and Homoptera which include aphids, leafhoppers, white flies, mealy bugs, cicadas and scale insects. It is a theory of the invention that the insects which are susceptible to treatment with the subject formulations are those which harbor symbiotic bacteria in their gut. Accordingly, after insects than those listed which harbor symbiotic material can also be controlled with the subject formulations. Other target organisms include arachnoids, particularly spider mites (arthropoda).

Plants which are colonized by the pathogenic organisms include flowering plants, grasses, including bent grass, vegetables, cereals and fruits including tomato, potato, artichoke, strawberries, corn, cereal grains, onion, cucumber, lettuce, tobacco, and citrus such as orange, lemons, limes and grapefruit, as well as bell peppers and grapes, and fruit trees such as peach, apple and cherry. Also of interest are ornamentals such as roses and trees, particularly conifers. Also included are crops intended for consumption by fowl and animals, including humans, directly or indirectly. By "directly or indirectly" is intended that the crops could be ingested, for example, by humans (direct consumption), or that it is the nonhuman animal or fowl which ingests the crop and is in turn ingested by humans (indirect consumption). Crops intended for consumption include tobacco, animal and fowl fodder, crops intended for processing into alcohol or food products such as corn syrup, and the like.

Of particular interest is treatment of plants affected by powdery mildew which is caused by species of fungi of the family Erysiphaceae. Generally the genera are distinguished from each other by the number (one as opposed to several) of asci per cleistotheciun and by the morphology of hypal appendages growing out of the walls of the creistothecium. As an example the following genera cause powdery mildew in the indicated plants: *Erysiphe cichoracearum*, begonia, chrysanthemum, cosmos, cucurbits, dahlia, flax, lettuce and zinnia; *E. graminis,* with cereals and grasses; *E. polgoni,* beans, soybeans, clovers, and other legumes, beets, cabbage and other crucifers, cucumber and cantaloupe, delphinium and hydrangea; *Microsphaera alni,* blueberry, catalpa, elm, lilac, oak, rhododendron, and sweet pea; *Phyllactinia sp.* catalpa, elm, maple and oak; *Podosphaera leucotricha,* apple, pear and quince; *P. oxyacanthae,* apricot, cherry, peach and plum; *Spaelrotheca macularis,* strawberries; *S. mors-uvea,* gooseberry and currant; *S. pannosa,* peach and rose; and *Uncinula necator,* grape, horse chestnut and linden.

Also of particular interest is the treatment of plants affected by rust caused by Basidiomycetes of the order Uredinales. These plant rusts are among the most destructive of plant diseases. They have caused famines and ruined the economics of large areas, including entire countries. There are about 4,000 species of rust fungi. The most important rust fungi and the diseases they cause follow: Puccinia, causing severe and often catastrophic diseases on numerous hosts such as the stem rust of wheat and all other small grains (*P. graminis*); yellow or stripe rust of wheat, barley and rye (*P. striiformis*); leaf or brown rust of wheat and rye (*P. recondita*); leaf or brown dwarf rust of barley (*P. border*); crown rust of oats (*P. coronata*); corn rust (*P. sorghi*); southern or tropical corn rust (*P. polysora*) sorghum rust (*P. purpurea*); and sugarcane rusts (*P. sacchari* and *P. kuehnii*).

Puccinia also causes severe rust diseases on field crops such as cotton (*P. stakmanii*); vegetables such as asparagus (*P. asparagi*); and flowers such as chrysanthemum (*P. chrysanthemi*), hollyhock (*P. malvacearum*), and snapdragon (*P. antirrhini*). Gymnosporangium, causes the important cedar-apple rust (*G. juniperi-virginianae*) and hawthorn-cedar rust (*G. globosum*). Hemileia, causes the devastating coffee leaf rust. (*H. vastatrix*). Phragmidium, causes rust on roses and yellow rust on raspberry.

Uromyces: several species cause the rusts of legumes (bean, broad bean, and pea) and one causing rust of carnation (*U. caryophyllinus*). Cronatrium, causes several severe rusts of pines, oaks, and other hosts, such as the white pine blister rust (*C. ribicola*); fusiform rust of pines and oaks (*C. quercuum* f. sp. *fusiform*); eastern gall or pine-oak rust (*C. quercuum* f. sp. *virginianae*); pine-sweet fern blister rust (*C. comptoniae*); pine-Comandra rust (*C. comandrae*); and southern cone rust (*C. strobilinum*). Melampsora, causes rust of flax (*M. lini*). Coleosporium, causes blister rust of pine needles (*C. asterinum*). Gymnoconia, causes orange rust of blackberry and raspberry. Phakopsora, causes the potentially catastrophic soybean rust (*P. pahyrhizi*). Tranzschelia, causes rust of peach.

For treatment of powdery mildew, rust and other pathogens which colonize the leaves of the host plant, the host plants are sprayed to run off with a formulation of the invention. The plants can be sprayed prior to or after infestation, preferably prior to infestation. However, in order to minimize damage to the host plant, where feasible, it is preferable to treat older plants, as young green leaves tend to be more susceptible to phytotoxicity.

Also of particular interest is treatment of phylloxera infestation in grapes. For this application, it is necessary to deliver the formulation deep into the rhizosphere to the location of the insect colony. Typically, phylloxera are found as deep as the roots of the host plant, which may be eight feet or deeper. When used in a solid form or microencapsulated, the dosage used is typically on the order of 1% to 35% on a w/w basis, the maximum loading to be determined as a function of shell material selected. Analytical chemical techniques are used to determine and optimize rate of release. For qualitative purposes GC techniques can be used to determine the amount of aldehyde released. The samples of encapsulated (pelletized) product are mixed with the soil types selected and sampled at different time periods to measure release. Alternatively, volatile gases released from the formulation can also be analyzed. For measuring the activity of foliar and drip irrigation applications the stability of the formulations over time can also be evaluated using the GC methodology using methods known to those skilled in the art. Methanol or alcohol extractions of the formulations also can be prepared for HPLC analysis.

When used to control the level of a toxic by-product produced by pathogen, the material and/or target organism can be treated using the methods and compositions of the invention. As an example, material in which the level of mycotoxin can be controlled can either be consumable or non-consumable and is preferably a plant or of plant origin, although any other material contaminated with fungi which produce microbial toxins or is capable of being colonized by or supporting the growth of toxin producing microorganisms is suitable. Of particular interest are crops intended for consumption by fowl and animals, including humans, directly or indirectly. By "directly or indirectly" is intended that the crops could be ingested, for example, by humans (direct consumption), or that it is the nonhuman animal or fowl which ingests the crop and is in turn ingested by humans (indirect consumption). Crops intended for consumption include tobacco, animal and fowl fodder, crops intended for processing into alcohol or food products such as corn syrup, and the like. Plants and plant materials colonized by toxin producing fungi include, for example, barley and other grasses, rice, corn, wheat, oats, hops, cassava, beans, potato, peanuts, sweet potato, tomato, sugar cane, coconut, citrus, grapes, sorghum, melons, cucumber, lettuce, spinach, artichoke, onion, tomato, strawberry and tobacco.

The level of mycotoxin also can be controlled in products derived from plant materials, such as processed juices, corn products such as high fructose corn syrup, oil, meal, starch, alcohol and products containing these and other corn derived ingredients and tobacco products such as cigars, cigarettes, and smokeless tobacco by inhibiting or preventing growth of toxin-producing fungi in the materials from which these items are produced either pre- or postharvest. Similarly, microbial toxin levels also can be controlled in forage grasses such as fescue, bent grass, alfalfa, clover, and tuff grasses and in commercially prepared animal feeds including those for cattle, sheep, pigs, and horses; fowl such as turkeys and chickens; fish such as trout, catfish and salmon; domestic pet foods including dog and cat foods; and laboratory animal foods by treatment pre- or postharvest of the materials themselves or precursor materials.

Moreover, when using the preferred compounds of cinnamic aldehyde, coniferyl aldehyde, Tween 80, NaHCO$_3$ and saponin from yucca, there is likely to be little toxicological risk to the consumer or handler from any horticultural or food crop treated with these compounds since they are common to the food industry. Similarly, as these compounds leave no toxic residue, there is little chance of any detrimental effect on the wider environment, and their use is likely to be compatible with current biological control methods.

The following examples are offered by way of illustration and not by way of limitation.

EXAMPLES

EXAMPLE 1

Treatment of Powdery Mildew On Rose Cultivars

Potted Roses

Eight cultivars of rose were used to investigate the effect of a cinnamic aldehyde/NaHCO$_3$ formulation on rust and spores. The cultivars used included Moss unnamed (Moss), Galica, Rosette Delize (Hybrid Tea), Rosa Rugosa Rubra (Rugosa), Abel Morrison (Hybrid perpetual), John Laing, Betty Prior, and Rose de Roi. Five (5) potted cultivars (Moss, Galica, Hybrid Tea, Rugosa, and Hybrid perpetual) were selected and assigned a disease rating after Paulus and Nelson (supra) for powdery mildew, rust and spores.* The Moss and Galica cultivars were 5 on a scale of 0–5 (where 0=no powdery mildew rust/spores lesions, 1=1–25, 2=26–50, 3=51–75, 4=76–90, and 5=>90% total leaves per bush). The Hybrid Tea and Hybrid perpetual were rated 3 and the Rugosa was rated 1. The Moss and Galica also were infected with rust equivalent to a 3 rating.

*Spores were evaluated only on Moss, Galica and the control plants.

Each cultivar received a foliar spray of about 100 ml of a cinnamic aldehyde formula containing 5 g cinnamic aldehyde, 80 g NaHCO$_3$, 10 g of Tween 80 and water to 1000 g. In addition, 250 ml of 0.01% (v/v) aqueous solution of 10° brix saponin extract from the *Yucca schidigera* plant was administered to each potted plant once a week beginning with the date of the first cinnamic aldehyde/NaHCO$_3$ treatment. Control plants received no treatment. A single treatment was eradicative of powdery mildew, rust, and spores through the final weekly field observation eight weeks later as compared to the no treatment controls which remained at disease ratings of 5, 3, and 4 for powdery mildew, rust and spores, respectively. Moreover, the treatment appeared to have induced systemic resistance. No phytoxicity was observed.

Field Grown Roses

Another experiment was designed for field grown cut flower rose to evaluate the efficacy of powdery mildew control by cinnamic aldehyde/NaHCO$_3$ during the same period (season) and environmental conditions. Powdery mildew and rust inoculum were high in the test field, and no additional inoculum was necessary to provide disease pressure. Cultivars John Laing, Betty Prior, and Rose de Roi were used in this investigation. Eight John Laing plants from a block row of sixteen were selected for treatment. Every other plant beginning with the first plant in the row was treated. Three Betty Prior plants were selected from a block of six were similarly treated, as were two Rose de Roi plants from a block of four. A single foliar spray treatment (about 100 ml) of a cinnamic aldehyde 5 g, and Tween 80, 10 g and NaHCO$_3$ 80 g and water to 1000 g was applied to each setting of cultivars. Plants were an average of 0.86 ml apart. The disease rating was the same as that used to evaluate powdery mildew in containerized cultivars. Controls were untreated plants. Absence of wind and exact spraying protected controls from spray drift. The John Laing cultivars were young, 45-day-old plants with a rating of 5 for powdery mildew. The Betty Prior cultivars were older ($\geq$240 days), previously sprayed with Eagle (120 days prior) with a rating of 3 for powdery mildew and the Rose de Roi were 240-days-old plants with a rating of 2 for powdery mildew and 2 for rust using the same scale as provided above. Induced systemic resistance was determined by observing the number of lesions of powdery mildew and rust produced on each plant after treatment as compared to untreated controls. Weekly reviews were made of the various plants. The effect on growth increase of the treatment regimen was determined at the last field observation of each plant.

With the exception of the untreated controls and three plants of cultivar Betty Prior which had reinfection of powdery mildew with a rating of 3, all plants were free of powdery mildew at the end of the five week trial. No phytotoxicity was observed. All plants had new growth exceeding that of the untreated controls.

The Mean Percentage of Disease Control (MPDC) was calculated for even group of plants. The results were as follows for powdery mildew: John Laing, 98.3%; Betty Prior, 64.3%; Rose de Roi, 100%. The average for all three roses was 90.7% for powdery mildew. Rust was evaluated only on Rose de Roi, and was 85.0%. Effective fungicides for powdery mildew should provide a MPDC of ≧70% under Greenhouse or field conditions, and for rust ≧65%.

To evaluate the efficacy of powdery mildew control by cinnamic aldehyde/NaHCO$_3$ in combination with saponin for field grown cut flower rose, a 250 ml of 2% (v/v) aqueous solution of 10° brix saponin extract from *Y. schidigera* is administered to each plant beginning with the date of the first cinnamic aldehyde/NaHCO$_3$ treatment as described above and the MPDCs calculated.

EXAMPLE 2

Treatment of Fungi and Insects on Roses with Coniferyl Aldehyde

Six cultivars of infected rose in dedicated experimental rose gardens were used. Four of Mrs. John Laing (Hybrid perpetual) and two of Marchionese of Londonderry (Hybrid perpetual) were treated with one of two formulations of coniferyl aldehyde. The low dose treatment (T1) was a coniferyl aldehyde, 10 g of Tween 80, 80 g of NaHCO$_3$ and 905 g of H$_2$O for 1000 g of product. The high dose treatment (T2) was a coniferyl aldehyde formula comprising of 100 g of coniferyl aldehyde, 20 g Tween 80, 120 g NaHCO$_3$, 760 g H$_2$O for 1000 g of product. See Table 1.

The first two Mrs. John Laing plants (P1 and P2) were assigned a disease rating of 3 for powdery mildew and rust after Paulus and Nelson (supra). Mrs. John Laing plants 3 and 4 (P3 and P4) were assigned a disease rating of 4 and 5 respectively for powdery mildew and rust. P3 and P4 also were infected with aphids, each plant with>35 insects. Both Marchionese of Londonderry (P5 and P6) were rated 5 for powdery mildew and rust after Paulus and Nelson (supra). Two treatment formulae were used for this screen trial. Each plant (P1 through P6) received a ≈100ml treatment spray of as shown in the Table 1 below. Control plants received no treatment (i.e., they were sprayed with water alone). The change in the rating (PRE-POST) was calculated as the mean percentage of disease control (MPDC). MPDC is defined by the formula:

MPDC is defined by the formula:

$$MDIC = \frac{(MDIC - MDIT)}{MPDC} \times 100$$

and

MDIC=Mean % of disease incidence in untreated controls
MDIT=Mean % of disease incidence in the treatment

TABLE 1

| Plant - Treatment/Dose Assignment | |
|---|---|
| Treatment/Dose | Plant |
| T1 - Low | P1, P4, P6 |
| T2 - High | P2, P3, P5 |

As shown in Table 2 below, both formulas reduced (Pre-Post treatment change) levels of infection. Both powdery mildew and rust levels of infection were reduced a minimum of one rating category after treatment as compared to plants sprayed with water alone.

TABLE 2

| | Plant Treatment/Dose | | | | | |
|---|---|---|---|---|---|---|
| | Low (T1) | | | High (T2) | | |
| | P1 | P4 | P6 | P2 | P3 | P5 |
| PEST | | | | | | |
| Powdery Mildew | | | | | | |
| Pre | 3 | 3 | 4 | 5 | 5 | 5 |
| Post | 2 | 1 | 1 | 2 | 1 | 1 |
| Change | 1 | 2 | 3 | 3 | 4 | 4 |
| Rust | | | | | | |
| Pre CFU | 3 | 3 | 4 | 5 | 5 | 5 |
| Post CFU | 2 | 1 | 3 | 2 | 1 | 1 |
| Change | 1 | 2 | 1 | 3 | 4 | 4 |
| Aphids | | | | | | |
| Pre # | — | 35 | — | — | ≧35 | — |
| Post # | — | 0 | — | — | — | — |
| Change | — | ≧35 | — | — | ≧35 | — |

Aphids were eliminated from P3 and P4 indicating that the formulas have insecticidal properties. Coniferyl aldehyde, as is cinnamic aldehyde, shared antibiotic properties and may eliminate symbiotic bacteria present in the host insect without which the insect cannot live.

Evaluation of treatment of fungi and insects on roses with coniferyl aldehyde in combination with saponin treatment are conducted essentially as above. Cultivars of infected rose are treated with one of two formulations of coniferyl aldehyde (low dose treatment (T1) and high dose treatment (T2)) in combination with a 2% (v/v) aqueous solution of 10° brix saponin extract from *Y. schidigera* administered to each plant beginning with the date of the T1 and T2 treatments.

EXAMPLE 3

Treatment Of Powdery Mildew On Rose

A three treatment experiment with cinnamic aldehyde formula and components, coniferyl aldehyde formula and combined cinnamic and coniferyl aldehyde formula was evaluated on field grown roses known to be susceptible to powdery mildew. The plants were blocked by variety before fungitide treatments and were randomized as to the plants. Two varieties were used in each of the three experiments described below. In experiment 1, Reichsprasident von Hindenfurg (Bourbon) and Oskax Cordel (Hyvfid Perpetual) were used; in experiment 2, Rosa Gallica Officinalis (Apothecary Rose) and Deuil de Paul Fontaine (Hybrid Moss) were used. In experiment 3 Comte de Chambord (Portland) and Madame Pierre Oger (Bourbon) were used. Experiment 1 evaluated the effect of Cinnamic aldehyde alone and in combination with Tween 80 and/or NaHCO$_3$ components, experiment 2 evaluated the effect of Coniferyl aldehyde, and experiment 3 evaluated a combination of cinnamic aldehyde and coniferyl aldehyde with Tween 80 and/or NaHCO$_3$. Nine treatments were tested in experiment 1, six in experiment 2 and six in experiment 3. See Table 3.

Each plant received a single foliar spray of 100 ml following evaluation of powdery mildew infection (after Paulus and Nelson). The response variable recorded for each plant was the powdery mildew infection rating based on the Paulus/Nelson rating scale. Plants were evaluated on this scale just prior to and four days after treatment. Mean percentage of disease control data indicate that all three combination formulas (i.e., G, M, and Q) provided in excess of 70% disease control based on these experiments. See Table 4. Treatment Q was significantly better than all other treatments, including benomyl.

The above three treatment experiment in combination with saponin is performed with the following modifications. The cinnamic aldehyde formula and components, coniferyl aldehyde formula and combined cinnamic and coniferyl aldehyde formula is evaluated on field grown roses known to be susceptible to powdery mildew following the above protocols and in combination with a 250 ml of 2% (v/v) aqueous solution of 10° brix saponin extract from *Y. schidigera* administered to each plant beginning with the first date of treatment.

phylloxera mortality occurs during this activity. Low dose concentrations of formulae may be protective of grape stock roots by disrupting the "search and identify feeding site" behavior of the insect. All three types of effects are evaluated using the following protocols.

Adult and Nymphal Mortality Experiment

Approximately twenty four eggs of phylloxera are allowed to develop for up to 30 days on standard excised grape roots. At around 30 days, some of the insects are nymphs while others are adults. New eggs are removed during the process. Insect infected roots are submerged into a test formula for 6 seconds then set aside to dry in the air. The test formula is applied as a single solution or consecu-

TABLE 3

Treatment Protocol

| Group | Treatment | Ingredient(s) | Amount of treatment ingredient(s) (balance H2O to 1000 g) |
|---|---|---|---|
| 1 | A | Cinnamic aldehyde (CNMA) | 5 g |
| 1 | B | Tween 80 (T80) | 10 g |
| 1 | C | NaHCO$_3$ | 80 g |
| 1 | D | CNMA + T80 | 5 g, 10 g |
| 1 | E | CNMA + NaHCO$_2$ | 5 g, 80 g |
| 1 | F | NaHCO$_3$ + T80 | 80 g, 10 g |
| 1 | G | Formula 1 | A = 5, B = 10 g, C = 80 g |
| 1,2,3 | H | +Control (Benomyl) | per manufacture instructions |
| 1,2,3 | I | −Control | no treatment |
| 2 | J | Coniferyl aldehyde (COFA) | 5 g |
| 2 | K | COFA + T80 | 5 g, 10 g |
| 2 | L | COFA + NaHCO$_3$ | 5 g, 80 g |
| 2 | M | Formula 2 | J = 5 g, B = 10 g, C = 80 g |
| 3 | N | CNMA + COFA | 2.5 g, 2.5 g |
| 3 | O | CNMA + COFA + T80 | 2.5 g, 2.5 g, 10 g |
| 3 | P | CNMA + COFA + NaHco$_3$ | 2.5 g, 2.5 g, 80 g |
| 3 | Q | Formula 3 | A = 2.5 g, J = 2.5 g, B = 10 g, C = 80 g |

TABLE 4

Effect of Cinnamic Aldehyde and Coniferyl Aldehyde Formulations on Rose Powdery Mildew

| | Mean % Disease Control Aldehyde | | | |
|---|---|---|---|---|
| Additive Formulation | None | Cinnamic Aldehyde (5 g) | Coniferyl Aldehyde (5 g) | Cinnamic Aldehyde (2.5 g) + Coniferyl Aldehyde (2.5 g) |
| None | 0% | 50% | 56% | 69% |
| T80 (10 g) | 0% | 44% | 44% | 69% |
| NaHCO$_3$ | 44% | 56% | 44% | 88% |
| T80 + NaHCO$_3$ | 19% | 94% | 81% | 100% |
| Benomyl | 79% | NT | NT | NT |

EXAMPLE 4

Treatment of Grape Phylloxera with Cinnamic Aldehyde and/or Coniferyl Aldehyde alone and/or with Tween 80 and/or NaHCO$_3$, and/or Saponin Feeding Site Location Test Mortality resulting from physiological process disruption is determined by the Adult and Nymphal mortality experiment and by the Egg Hatch experiment. After hatching, new insects must secure a verified appropriate feeding site. This activity must be successful if the life cycle of the insect is to continue. Research indicates that approximately 80% of tively. Alive insects as defined by growth, oviposition or limb movement is determined after 5 days. An insect is considered dead if it abandons its feed site. Water control and three dosages of a test formula are evaluated with 4 to 5 replicates of two roots for each treatment. Concentrations that cause greater than 95% mortality are determined. Probit analysis is conducted if appropriate. (See Table 5).

TABLE 5

Effect of Cinnamic Aldehyde and Coniferyl Aldehyde Formulations on Phylloxera Egg Mortality (Percent)

| | Aldehyde | | | |
|---|---|---|---|---|
| Additive Formulation | None | Cinnamic Aldehyde (20 g) | Coniferyl Aldehyde (20 g) | Cinnamic Aldehyde (10 g) + Coniferyl Aldehyde (10 g) |
| | Percent Died in Shell | | | |
| None | 0 | 100 | 100 | 100 |
| T80 (10 g) | 0 | 100 | 100 | 100 |
| NaHCO$_3$ | 0 | 100 | 100 | 100 |
| T80 + NaHCO$_3$ | 0 | 100 | 100 | 100 |
| Saponin (1% 10 brix) | 0 | 100 | NT | NT |
| Saponin + T80 | 0 | 100 | NT | NT |
| Saponin + NaHCO$_3$ | 0 | 100 | NT | NT |
| Malathion | 0 | NT | NT | NT |
| Carbofuran | 0 | NT | NT | NT |

Egg Hatch Experiment

Mixed age groups of about 55 grape phylloxera eggs are established on filter paper and treated with a select concentration of a test formula. After one week, the percentage of hatch is determined. The rising portion of the dose-response line using a range of doses (100 to 2000 pm, or 0.1 to 2 g/l) with a single group of eggs at each dosage constitutes a dose-setting experiment. Three replicates of the experiment using 3 to 5 dosages on the rising portion of the dose-response line is conducted over time. LD50 and LD95 are determined by probit analysis. These trials are conducted with eggs having a narrow range of ages.

Approximately twenty phylloxera eggs are placed on standard excised grape roots that have been dipped for 7 seconds a particular in concentration of test formula, then air dried. The test formula is applied as a single solution or consecutively. After 25 days the number of live insects is evaluated. Three replicates of 5 roots for each treatment are evaluated for three dosages and a watercontrol. The concentration which prevents 95% of the insects from surviving is determined.

EXAMPLE 5

Protocol for Aphid, Spider Mite and White Fly

Activity of cinnamic aldehyde and/or coniferyl aldehyde and/or in combination with saponin against black bean aphid, *Aphid fabae*, two-spotted spider mite, *Tetranychus urticae*, and silvefieaf white fly, *Bemisia argentifolii* is determined as follows:

Petri Dish Bioassay

Each petri dish (60 mm diameter) is treated with a specific rate of product (e.g., 10–1000 ppm) dissolved in water and/or with one of a serial dilution of a 10° brix saponin extract from *Y. schidigera* ranging from 0.001%–1% (v/v) aqueous solution, which is then allowed to dry. Twenty specimens of each arthropod are put in each dish, (replicate 10 times). The mortality after three hours in contact with a treated plated, is compared to that of arthropods in petri dishes treated only with diluent.

Plant Foliar Bioassay

Plants are grown in 7.5 mm pot in potting soil in greenhouse. Cotton plants are used for spider mites and white fly and sugar beets are used for aphids. When plants reach 3 leaf stage, they are infested with 60 of the specified arthropod (6 replications). The insect/mite is allowed to settle and feed. The plant is sprayed to runoff with a formulation containing 100 to 2000 pm, or 0.1 to 2 g/l concentration of a test formulation. When the test formulation is to include saponin, the plant is sprayed to runoff with a 0.05%to 1% (v/v) aqueous solution of 10° brix saponin extract from *Y. schidigera*. The plant is covered with tall plastic cage (5 mm tall×10 mm diameter). The mortality after three days of the insect/mites on the plants sprayed with a test formulation is determined and compared with that of insect/mites on plants sprayed only with after.

EXAMPLE 6

Treatment of Root-Knot Nematode (*Meloidogyne javanica*)

In a double blind test, concentrations of the formulation were screened for activity against root-knot nematode, *Meloidogyne javanica*. Nematodes were put in direct contact with the chemical and, at 24 hour intervals, mortality was assessed both visually and by probing. *Meloidogyne javanica* was produced using hydroponics. The nematodes were harvested and used within 24 hours.

Approximately 100 nematodes in 0.07 mls of water were pipetted into a syracuse dish (Fisher) and 1 ml of test formulation was immediately pipetted into each dish. The dishes were then placed into plastic bags to retain moisture and prevent evaporation. For syracuse dishes were used for each solution test formulation. Every 24 hours for 7 days, the solutions were examined and the first 10 nematodes encountered were assessed as either living or dead. This was based on morphological integrity of the nematode and touch. Moving nematodes were counted as living. As concentrations greater than 100 ppm cinnamic aldehyde in vehicle (2% Tween 80, 6% $NaHCO_3$) 100% nematodes were dead at 24 hours. AT 10 ppm, 0%, 15%, 17.5%, 22.5%, 27.5%, 52.5% and 52.5% were dead at 24, 48, 72, 96, 108, 132 and 156 hours, respectively. There was no effect on mortality at 1 ppm and 0.1 ppm cinnamic aldehyde in vehicle. Addition of a 1:60 dilution 10° brix concentrate of *Yucca schidigera* saponin (0.86 ml of 10° brix concentrate in water diluted in 50 ml of test formulation), resulted in 100% mortality at 24 hours with the lowest concentration of cinnamic aldehyde in vehicle tested, 0.1 ppm. However, saponin alone had the same effect, Reagent alcohol (90% EtOH, 5% MeOH, 5% 1PA) killed all nematodes at 24 hours. Minimal effect of the vehicle on mortality was observed: 2.5% at 72 hours and 5% at 108 hours.

EXAMPLE 7

Treatment Of Strawberry Red Core (*Phytophthora Fragariae*)

Strawberry red core disease is caused by the fungus *Phytophthora fragariae* Hickman which is spread by means of infected planting material or soil infested with long-lived oospores of infected debris.

Various formulations containing cinnamic aldehyde and/ or coniferyl aldehyde are tested as follows: Macerated strawberry roots infected with *Phytophthora fragariae* are thoroughly mixed with infested compost and allowed to decompose for 4 to 6 weeks to produce a well rotted inoculum for treatment. This is divided into 1 kg lots and mixed with 1500 ml of a test formulation at different concentrations. After 10 minutes treatment, the compose is rinsed under running tap water on a 25 mm sieve for a minimum of 5 minutes to remove all traces of the test formulation. The compost is then put into 9-era diameter plastic pots and planted with 4 strawberry plants per pot. Five pots are used for each treatment. Plants are grown in a controlled environment room at 15° C. and 18 h day length; the compost is kept damp to encourage infection. Pots are placed on grids to avoid cross infection among treatments.

After 9 weeks the strawberry plant roots are washed free of compost and examined for signs of infection by cutting roots longitudinally and looking for red steles, and rotted or brown roots. All infections are confirmed by microscope examination of root pieces for the presence of oospores of *Phytophtora fragariae*.

EXAMPLE 8

Treatment of Fungal Pathogens on Corn

A three treatment experiment with cinnamic aldehyde formula and components, coniferyl aldehyde formula and combined cinnamic and coniferyl aldehyde formulas is evaluated in combination treatment with a 0.05% to 1% v/v aqueous solution of 10° brix saponin extract from *Y. schidigera* on field grown corn known to be susceptible to pathogenic fungal infestation. The plants are blocked by variety before fungicide treatments and are randomized as to the plants. Various varieties susceptible to fungal infestation are tested using the following protocol which evaluates the effect of cinnamic aldehyde and/or coniferyl aldehyde alone and in combination with Tween 80 and/or $NaHCO_3$, and/or saponin.

Each plant receives a single foliar spray to run off following evaluation of fungal infection (after Paulus and Nelson). The response variable recorded for each plant is the fungal infection rating based on the Paulus/Nelson (supra) rating scale. Plants are evaluated on this scale just prior to and four days after treatment.

EXAMPLE 9

Pitch Canker Disease

Pitch canker disease, caused by the fungus *subglutinans* f. sp. *pini* is characterized by a resinous exudation on the surface of shoots, branches, exposed roots and boles of infested trees. The host and geographic range of the pitch canker pathogen has greatly increased since it was first discovered in California in 1986. The pathogen has recently been discovered in Mexico and Japan. An association of Engraver beetles (Scolytidae: IPS species) as vectors of the Pitch Canker Fungus has been made by Fox, et al., (1991).

Bioassay based on inhibition of radial growth of *Fusarium subglutinans* f. sp. *pini*, (pitch canker pathogen).

Under sterile conditions 8 ml of the formulation with CNMA at the concentrations shown in Table 6 were pipetted into 200 ml of molten 2% potato dextros agar (PDA), the mixture was dispersed into five plastic petri dishes (25 ml dish). Each of four plates was inoculated at the center with an agar plug transferred from a growing PDA culture of *Fusarium subglutinans* f. sp. *pini* (isolate SL-1). A fifth plate was left noninoculated as a control. Benamyl (5 ppm) was used as a positive control. All inoculated and non-inoculated plates were incubated at 18° C. for five days, after which colony diameters were measured.

Results

Table 6 shows raw data averages for bioassay. Table 7 compares CNMA PGXL formula, CNMA PGXL formula+ saponin *Yucca schidigera* extract 10° BRIX) @0.86 ml, against controls.

TABLE 6

Radial Growth of *F. Subglutinans* f. sp. pini

| | Treatments | |
|---|---|---|
| | PGXL CNMA colony diameter (cm) | PGXL CNMA + Saponin (.86 ml) colony diameter (cm) |
| ppm | | |
| 10 | 4.36 | 4.09 |
| 100 | 4.24 | 4.3 |
| 2,500 | 3.51 | 3.6 |
| 5,000 | 2.98 | 2.91 |
| 12,500 | 0 | 0 |
| 25,000 | 0 | 0 |
| Controls | | |
| 2% Glutaraldehyde | 3.66 | |
| $H_2O$ | 3.74 | |
| 5 ppm Benomyl | 0 | |
| PDA (unamended) | 4.04 | |

EXAMPLE 10

Synergist Bioassay

The synergistic effect of a compound is essentially determined following the protocols described in Example 3, Tables 3 and 4, and each of the above Examples. An effective amount of a synergist test compound is added or applied separately in combination with a given formulation in a serial dilution and concentration regime ranging from control levels devoid of the synergist test compound to a concentration that is well above optimum. The antipathogenic and/or phytotoxic effect of a particular synergist test compound on a given pathogen and/or plant host is measured for each formula and component with or without a serial diluent of the synergist test compound following essentially the protocols of the above Examples. Optimal dose-range is calculated in vitro and in vivo from control dose levels to saturation dose levels in which a further increase in one controlling variable produces no further positive increase in the resultant effect. The effectiveness of each test formulation is measured by comparing to control formulations lacking of the synergist test compound and MDICs and MDITs calculated. Synergist compounds are identified which provide: a mean disease resistance for a particular formulation of at least about 60% or better with an optimum of about 70% or greater; and/or a phytotoxicity rating of 2 or less, with 1 or less being optimum.

Saponin Bioassay

A saponin or saponin extract is admixed or applied as a separate solution in combination with a given formulation in a serial dilution regime ranging from control levels with 0% saponin and 100% other component through equal and then saturation level of each component. The synergistic effect of the formulation is measured by examining the antipathogenic and phytotoxic effect of a particular pathogen and/or plant host to each formula and component with or without a serial diluent of saponin following the protocols of the above Examples. An effective amount of saponin is measured by comparing to an equivalent in activity of a saponin extract control from *Y. schidigera* comprising 0.05% to 1% v/v aqueous solution of 10° brix saponin extract. Optimal dose-range for a given formulation is calculated in vitro and in vivo. The effectiveness of each test formulation is measured by comparing to formulations devoid of saponin. Saponins having synergistic properties are identified which provide: a mean disease resistance for a particular formulation of at least about 60% or better with an optimum of about 70% or greater; and/or a phytotoxicity rating of 2 or less, with 1 or less being optimum.

EXAMPLE 11

Materials and Methods

Experiment 1

The contact molluscicidal bioassay studies were carried out by a substrate contact method. For liquid formulation, filter paper discs (15 cm in diameter) were dipped in test solutions for 2 seconds and subsequently air dried. For dry formulations, substrates were placed on filter paper discs to a depth of 0.5 cm. Dry substrate (e.g., saponin fiber, mill run) were wetted with 10 ml of formula. Discs were placed on the bottom of paper plates (25 cm diameter) the rims of which had been coated with petroleum jelly and NaCl to prevent animal escape from plates. Four snails (*Sephia hortensis*) from Connecticut Valley Biological and two slugs (*Deroceras reticulatum*) from Carolina Science were placed on the treated or piled discs in each replication (five replications). Experimental formulations were assigned as:

Formulation and Number Composition

1 F1- PGXL (2% Cinnamic Aldehyde, 2% T80, 6% NaHCO$_3$)
2 F2=Saponin (10° BRIX) and PGXL (1:9)
3 F3=Saponin Fiber+PGXL (to wet - 10 ml)
4 F4=Saponin Fiber+Wheat Mill Run (50/50 w)
5 F5=Saponin (10° BRIX) (to wet - 10 ml) and Wheat Mill Run
6 F6=Saponin Fiber
7 F7=PGXL Formula Blank (CNMA) to wet - 10 ml) and Wheat Mill Run
8 F8 =H$_2$O
9 F9=Lilly Miller "SSIKB" (Positive Control - Metaldehyde product)
10 F10=CNMA (encapsulated) in oil (Calgene cc-22F) emulsion, encapsulated CNMA @31.4+1.2% w/w in starch sucrose shell (85/15)

Experiment 2

The cinnamic aldehyde formula components were evaluated for activity as follows. Filter paper discs 7.5 cm in diameter were wetted completely with product or component and allowed to air dry. Discs were placed in bottom of "Mason ½ pint" glass jars. Two snails and one slug were put in each jar for 5 replications. Jars were sealed with cheese cloth and lid holder to permit respiration. Observations were made at 48 hrs.

Results and Discussion

In general, from Table 7, the formulations contained cinnamic aldehyde (PGXL) were effective molluscicides demonstrating 100% mortality at 48 hrs. The PGXL formula also performed as well as saponin based formula and had a higher percent mortality than the positive control (F9-"SSIKB"). Crude saponin fiber (F3-with PGXL) combined with CNMA achieved a high percent mortality early in the experiments, second only to encapsulated CNMA which was extremely lethal achieving 100% mortality in 30 minutes. Table 8 presents data from experiment 2 components for formula, negative control and related activity percentages.

TABLE 7

Data Analysis - Slugs and Snails
May 3, 1995

| Formula | | 0 | .5 | 2.5 | 24 | 48 |
|---|---|---|---|---|---|---|
| #1 PGXL (2% c) | Snails | 0 | 0 | 50 | 50 | 100 |
| | Slugs | 0 | 0 | 100 | 100 | 100 |
| #2 10° B + PGXL | Snails | 0 | 0 | 25 | 50 | 50 |
| | Slugs | 0 | 0 | 50 | 100 | 100 |
| #3 S. FIBER/PGXL | Snails | 0 | 0 | 75 | 75 | 100 |
| | Slugs | 0 | 100 | 100 | 100 | 100 |
| #4 S. FIBER + M.R. | Snails | 0 | 0 | 100 | 100 | 100 |
| | Slugs | 0 | 50 | 100 | 100 | 100 |
| #5 10° B + M.R. | Snails | 0 | 0 | 50 | 75 | 100 |
| | Slugs | 0 | 0 | 0 | 100 | 100 |
| #6 S. FIBER | Snails | 0 | 0 | 75 | 75 | 75 |
| | Slugs | 0 | 0 | 100 | 100 | 100 |
| #7 CNMA BLANK + M.R. | Snails | 0 | 0 | 0 | 0 | 0 |
| | Slugs | 0 | 0 | 0 | 100* | 100* |
| #8 NEG. CONT. (H$_2$O) | Snails | 0 | 0 | 0 | 0 | 0 |
| | Slugs | 0 | 0 | 0 | 0 | 100* |
| #9 POS. CONT. (SSIKB) | Snails | 0 | 0 | 0 | 50 | 75 |
| | Slugs | 0 | 0 | 0 | 100 | 100 |
| #10 CNMA ENCA + OIL | Snails | 0 | 100 | 100 | 100 | 100 |
| | Slugs | 0 | 100 | 100 | 100 | 100 |

*Animal Contacted Plate Rim (NACL)

TABLE 8

Grid CNMA
GASTROPODA

| Formulation | % Mortality (48 hrs.) |
|---|---|
| None | 100 |
| T80 | 0 |
| NaHCO$_3$ | 0 |
| T80 + NaHCO$_3$ | 0 |
| Formula | 100 |
| H$_2$O | 0 |

A Whatman filter paper disc (7.5 cm) was placed on the bottom of each petri dish. 3 ml of H$_2$O pipetted on to discs. Moss was sorted into groups of 5 (3 moss). Moss sections 3.5 cm×3.5 cm were taken from core of potted stock and placed on discs for all plates. Two 2 ml of test solutions sprayed on each related dish. Petri dishes left at ambient temperatures and areas of desiccation were observed at 24, 48 and 60 hours.

Data in Table 9 shows percentage of desiccation over time. In general, the Cinnamic aldehyde formulation showed the greater percentage of desiccation over time. While saponin was effective, it was not as active as cinnamic aldehyde in formulation.

Data in Table 10 shows percent activity from formula components.

TABLE 9

BRYOPHYTA (MOSS)
Percent of Desiccation (over time)

| | 0 | 24 hrs. | 48 hrs. | 60 hrs. |
|---|---|---|---|---|
| MOSS: DICRANUM | | | | |
| F1 | 0 | 15 | 40 | 90 |
| F2 | 0 | 10 | 40 | 80 |

TABLE 9-continued

BRYOPHYTA (MOSS)
Percent of Desiccation (over time)

|  | 0 | 24 hrs. | 48 hrs. | 60 hrs. |
|---|---|---|---|---|
| F3 | 0 | 15 | 50 | 85 |
| F4 | 0 | 5 | 15 | 25 |
| F5 | 0 | 6 | 18 | 26 |
| SPAGNUM (BOG MOSS) | | | | |
| F1 | 0 | 20 | 60 | 90 |
| F2 | 0 | 15 | 55 | 75 |
| F3 | 0 | 20 | 60 | 85 |
| F4 | 0 | 8 | 12 | 20 |
| F5 | 0 | 9 | 12 | 22 |
| WOODLAND: | | | | |
| F1 | 0 | 20 | 60 | 85 |
| F2 | 0 | 10 | 40 | 70 |
| F3 | 0 | 20 | 50 | 80 |
| F4 | 0 | 10 | 15 | 20 |
| F5 | 0 | 12 | 18 | 28 |

F1 PGXL (CNMA 2%)
F2 SAP (10° Brix)
F3 PGXL + SAP
F4 –CONTROL H$_2$O
F5 PGXL Formula Blank

TABLE 10

MOSS (60 hrs)

| Formulation | % Desiccation |
|---|---|
| None | 70 |
| T80 | 10 |
| NaHCO$_3$ | 20 |
| T80 + NaHCO$_3$ | 25 |
| Formula | 90 |
| Neg. Control | 10 |

As the above results show, potted roses or field grown roses sprayed to run off with an emulsion containing cinnamic aldehyde and sodium bicarbonate and concomitantly sprayed with saponin remained free of powdery mildew and rust for up to 56 days as compared to plants sprayed only with water. The plants also remained free of aphids. It has been reported that induced systemic resistance to powdery mildew of roses sprayed with Rubigon averages about 20 days. Mean disease control determinations of approximately 70% were obtained for roses sprayed with an aqueous solution of cinnamic aldehyde and coniferyl aldehyde or emulsions containing sodium bicarbonate and cinnamic aldehyde and/or coniferyl aldehyde. In parallel experiments, Benomyl gave a mean disease control of approximately 80%.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method for controlling growth of pathological organisms on plants, said method comprising:

contacting a plant with a formulation comprising one or more saponin compounds and an effective pathological organism growth modulating amount of one or more compounds of formula (2)

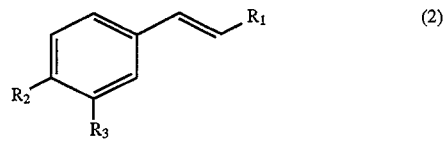

wherein R$_1$ represents —CHO, R$_2$ represents —H, —OH or an organic substituent containing from 1 to 10 carbon atoms, and R$_3$ represents —H, a methoxy group or organic substituent containing from 1 to 10 carbon atoms.

2. The method according to claim 1, wherein said growth modulating amount of formula (2) is 2.5 g/l to 12.5 g/l.

3. The method according to claim 1, wherein said growth modulating amount provides a mean disease resistance of about 70% or higher.

4. The method according to claim 3, wherein said growth modulating amount produces a phytotoxicity rating of 1 or less.

5. The method according to claim 1, wherein said one or more compounds are selected from the group consisting of cinnamic aldehyde and coniferyl aldehyde.

6. The method according to claim 1, wherein said formulation is free of antioxidants other than compounds of formula (2).

7. The method according to claim 1, wherein said plant is selected from the group consisting of a rose, grape, tomato, and bell pepper.

8. The method according to claim 7, wherein said pathological organism is selected from the group consisting of fungi, insects, arachnoids, and terrestrial mollusks.

9. The method according to claim 8, wherein said pathological organism is a fungus selected select from the group consisting of fungi which cause powdery mildew, rust, and botrytis.

10. The method according to claim 8, wherein said pathological organism is an insect selected from the group consisting of aphids and leaf hoppers.

11. The method according to claim 8, wherein said pathological organism is a terrestrial mollusks selected from the group consisting of snails and slugs.

12. Plants substantially free of fungal pathogens obtained according to the method of claim 1.

13. The method according to claim 1, wherein said formulation comprises at least one synergist.

14. The method according to claim 13, wherein said synergist is selected from the group consisting of a compound of the formula (1),

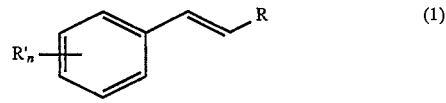

wherein R represents —CH$_2$OH or —CHO; n is an integer from 0 to 3; and each R independently represents OH or an organic substituent containing from 1 to 10 carbon atoms and from 0 to 5 heteroatoms, wherein the total number of carbon and heteroatoms in all R' substituents of said compound is no more than 15;

a compound of formula (2),

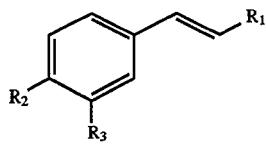

wherein $R_1$ represents —CHO, $R_2$ represents —H, —OH or an organic substituent containing from 1 to 10 carbon atoms, and $R_3$ represents —H, a methoxy group or organic substituent containing from 1 to 10 carbon atoms; cinnamic aldehyde; coniferyl aldehyde; an emulsifier; a salt of a polyprotic acid; and saponin.

15. The method according to claim 14, wherein said emulsifier is Tween 80.

16. The method according to claim 14, wherein said salt of a polyprotic acid is sodium bicarbonate.

17. The method according to claim 1, wherein said growth modulating amount of formula (2) is 0.01 to 25 g/l.

18. A composition comprising:

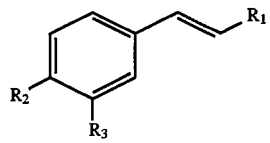

wherein $R_1$ represents —CHO, $R_2$ represents —H, —OH or an organic substituent containing from 1 to 10 carbon atoms, and $R_3$ represents —H, a methoxy group or organic substituent containing from 1 to 10 carbon atoms; and one or more saponins in an agriculturally compatible carrier to provide a mean disease resistance of about 70% or higher against a pathogenic organism which colonizes one or more plant surface.

19. The composition according to claim 18, wherein said growth modulating amount produces a phytotoxicity rating of 1 or less.

20. Seedlings substantially free of fungus obtained by the step of contacting said